United States Patent
Nielsen et al.

(10) Patent No.: US 7,289,204 B2
(45) Date of Patent: Oct. 30, 2007

(54) APPARATUS AND SENSING DEVICES FOR MEASURING FLUORESCENCE LIFETIMES OF FLUORESCENCE SENSORS

(75) Inventors: Hans Ole Nielsen, Lyngby (DK); Jan H. Hansen, Lyngby (DK); Kim P. Hansen, Lyngby (DK)

(73) Assignee: Delta Dansk Elektronik, Lys & Akustik, Horsholm (DK)

( * ) Notice: Subject to any disclaimer, the term of this patent is extended or adjusted under 35 U.S.C. 154(b) by 128 days.

(21) Appl. No.: 10/476,425

(22) PCT Filed: May 2, 2002

(86) PCT No.: PCT/DK02/00284

§ 371 (c)(1),
(2), (4) Date: Oct. 30, 2003

(87) PCT Pub. No.: WO02/090948

PCT Pub. Date: Nov. 14, 2002

(65) Prior Publication Data

US 2004/0090622 A1    May 13, 2004

(30) Foreign Application Priority Data

May 3, 2001 (DK) ............................. 2001 00696

(51) Int. Cl.
*G01J 3/30* (2006.01)

(52) U.S. Cl. .................................. 356/317

(58) Field of Classification Search ......... 356/317–318
See application file for complete search history.

(56) References Cited

U.S. PATENT DOCUMENTS

| | | | | |
|---|---|---|---|---|
| 5,030,420 A | * | 7/1991 | Bacon et al. ............. 250/458.1 |
| 5,094,819 A | * | 3/1992 | Yager et al. ................ 436/172 |
| 5,157,262 A | * | 10/1992 | Marsoner et al. ......... 250/458.1 |
| 5,315,993 A | * | 5/1994 | Alcala ........................ 600/341 |
| 5,606,170 A | * | 2/1997 | Saaski et al. ............ 250/458.1 |
| 6,045,756 A | * | 4/2000 | Carr et al. ............... 422/82.11 |
| 6,673,532 B2 | * | 1/2004 | Rao ............................... 435/4 |
| 6,818,437 B1 | * | 11/2004 | Gambini et al. ......... 422/82.08 |
| 2001/0034479 A1 | * | 10/2001 | Ring et al. .................. 600/322 |
| 2002/0187557 A1 | * | 12/2002 | Hobbs et al. ............... 436/161 |
| 2003/0068827 A1 | * | 4/2003 | Morris et al. ............... 436/136 |

* cited by examiner

*Primary Examiner*—Gregory J. Toatley, Jr.
*Assistant Examiner*—Kara Geisel
(74) *Attorney, Agent, or Firm*—Day Pitney LLP

(57) ABSTRACT

An apparatus and devices for measuring fluorescence lifetimes of fluorescence sensors for one or more analytes, the apparatus comprising (c) one or more reference systems (3,6,7), said reference systems each comprising one or more reference light sources (3) and being adapted to receive one or more excitation signals (1a), to produce reference optical signals (6b) in response thereto, and to produce one or more electrical reference output signals (7b) in response to one or more excitation signals (1a); and (d) or more phase detectors (10), said phase detections being adapted to detect one or more delays of said one or more electrical output signals of said one or more fluorescence sensor systems and said one or more reference systems, and to produce one or more phase output signals; and a method of measuring concentration of one or more analytes using such apparatus and/or devices.

29 Claims, 6 Drawing Sheets

APPARATUS AND SENSING DEVICES FOR MEASURING FLUORESCENCE LIFETIMES OF FLUORESCENCE SENSORS

BACKGROUND OF THE INVENTION

The present invention relates to an apparatus for measuring fluorescence lifetimes of fluorescence sensors for one or more analytes, fluorescence lifetime sensing devices for sensing fluorescence light of fluorescence sensors for one or more analytes, and a method of measuring concentration of said one or more analytes using such apparatus and/or devices.

In the present context, the terms analyte or analytes are intended to designate analytes in a broad sense including chemical substances such as biomolecules, blood gases e.g. $O_2$, $CO_2$; pH, salt ions e.g. $Na^+$ and $Cl^-$; and physical parameters such as temperature and pressure.

THE TECHNICAL FIELD

In biological and industrial processes, efficient control of the processes requires simultaneous monitoring of several key-parameters thereof, e.g. parameters such as temperature, pH, $PO_2$ and $CO_2$. Numerous sensor systems have been developed for such monitoring systems. However, they are usually based on commercially available discrete sensors, each of which is capable of sensing a single key-parameter. Consequently, there is a need for multi-analyte sensors capable of sensing several key-parameters simultaneously.

In particular in modern biotechnology relating to e.g. tissue engineering and genetic technology, cultivation is often performed in parallel systems with numerous batches being processed simultaneously. For efficient control of processes in such systems, a large number of analyses are required. Normally, such parallel systems require large process volumes. However, there is a trend to scale down process volumes to smaller volumes, e.g. less than 1 liter, to obtain more optimal process economy. For such smaller process volumes, however, even smaller sample volumes are required, often sample volumes of only few milliliters.

In addition, cultivation of tissues, cells, bacteria or other microorganisms in laboratories often uses small volume systems of less than 100 ml volume. Consequently, the sensors are required to be suitably small for use with such small sample volume.

Consequently, the use of conventional sensors is limited by both available physical space, small sample volumes and especially for parallel systems, the multiplication of sensors increasing costs. These factors combined have made precise process control unavailable for many applications.

Multi-analyte sensors based on measurement of fluorescence intensity measurements are known but they suffer from being influenced by drift of the intensity of the excitation source, photo-bleaching of active component of the sensor, and drift of detector efficiency.

Other multi-analyte sensors are based on fluorescence lifetime. These sensors solve the problem of sensitivity to drift in the opto-electronic components whereby the need for frequent re-calibrations is reduced.

In fluorescence lifetime based sensors, the chemical analytes are detected by measuring a change in the fluorescence lifetime of the utilized fluorophores. Fluorescent lifetime measurements are superior to intensity measurements in a number of aspects. Firstly, intensity drift in the excitation source and drift in the efficiency of the detectors do not affect the measurements. Secondly, photo-bleaching of the fluorophores only limits the total operational lifetime of the sensor (not the fluorescence lifetime of the fluorophore itself), and not the measurements. The sensor is operational as long as the sensor chemistry is capable of delivering a signal sufficiently high compared to the noise in the system. The need for re-calibration due to photo-bleaching is therefore reduced which is very important in e.g. industrial process monitoring applications where sensor systems are to be operated continuously for long periods of time.

There are mainly two ways of performing time-resolved fluorescence measurements; time-domain and frequency-domain measurements (see e.g. Lakowicz, Joseph R., Principles of fluorescence spectroscopy, Second Edition, Kluwer Academic/Plenum Publishers, New York 1999). Presently, the frequency-domain technique provides a robust and inexpensive technique with less stringent component demands compared to the time-domain technique.

When utilising frequency-domain fluorescence lifetime measurements where phase resolutions in the order of fractions of a degree is needed, the phase of the excitation source has to be known. Normally this is obtained by utilising phase stable excitation sources (e.g. large lasers) but this solution is not a suitable solution for a mass-produced industrial product. In such systems, light emitting diodes (LEDs) are more suitable, as they are compact, cheap and efficient.

They do, however, suffer from a bias current dependent phase, making precise lifetime measurements with LEDs very difficult.

PRIOR ART DISCLOSURES

EP 0 448 923 discloses a method, sensor and apparatus for detecting biological activities of a specimen by introducing a sample of the specimen into a sealed, transparent container containing a culture medium enabling metabolic processes in presence of microorganisms in the sample. Changes are monitored over time of concentrations of substances involved in the metabolic processes, e.g. $O_2$, $CO_2$ and pH. A change is measured in fluorescence intensity of at least one activable, inert fluorophore and at least one indicator component that changes their optical characteristics in response to changes in concentration of at least one such substance in the container. As these systems are bases on measurement of changes in fluorescence intensity, they are sensitive to drift in the intensity of the excitation source, photo-bleaching of the fluorophore and drift in detector efficiency.

WO 99/06821 discloses a method and apparatus for fluorometric determination of a biological, chemical or physical parameter of a sample comprising measuring the time or phase behaviour of at least two luminescent materials having different decay times wherein at least the luminescent intensity of one of the luminescent materials (the sensor luminophore) responds to the parameter to be determined and at least the luminescent intensity and decay times of the others of the luminescent materials (the internal reference luminophore) usually those having longer decay times does not respond to the parameter to be determined. The intensity of the luminescence of the internal reference luminophore functions as an internal reference for the intensity of the luminescence from the sensor luminophore whereby a second light source or a second light detector can be avoided.

DISCLOSURE OF THE INVENTION

Object of the Invention

It is an object of the present invention to seek to provide an improved method and apparatus for measuring concentration of one or more analytes.

It is another object of the present invention to seek to provide an improved apparatus for measuring fluorescence lifetime of fluorescence sensors for one or more analytes for which influences of drift of the intensity of the excitation source, photo-bleaching of active component of the sensor, and drift of detector efficiency are reduced.

It is still another object of the present invention to seek to provide such an improved apparatus for measuring fluorescence lifetimes of fluorescence sensors for one or more analytes simultaneously.

Further objects appear from the description elsewhere.

Solution According to the Invention

According to the present invention, these objects are fulfilled by providing an apparatus for measuring fluorescence lifetimes of fluorescence sensors for one or more analytes as defined in claim 1, the apparatus comprising
(a) one or more excitation light sources, said light sources being adapted to produce one or more excitation signals, and optionally further comprising beam adapting optics;
(b) two or more fluorescence sensor systems, said sensor systems each comprising one or more fluorescence sensors for sensing the one or more analytes and being adapted to receive said one or more excitation signals, to produce one or more optical sensor signals in response thereto, and to produce one or more electrical output signals in response to said optical sensor signals, said one or more electrical output signals being delayed with respect to said one or more excitation signals and being characteristics of the fluorescence lifetimes of the one or more fluorescence sensors;
(c) one or more reference systems, said reference systems each comprising one or more reference light sources and being adapted to produce one or more electrical reference output signals in response to said one or more excitation signals to receive said one or more excitation signals, to produce reference optical signals in response thereto, and to produce one or more electrical reference output signals in response to said one or more optical reference signals; and
(d) one or more phase detectors, said phase detectors being adapted to detect one or more delays of said one or more electrical output signals of said one or more fluorescence sensor systems and said one or more reference systems, and to produce one or more phase output signals.

It has turned out that by providing one or more reference systems, said reference systems each comprising one or more passive reference light sources and being adapted to produce one or more electrical reference output signals in response to said one or more excitation signals; and by providing one or more phase detectors, said phase detectors being adapted to detect one or more delays of said one or more electrical output signals of said one or more fluorescence sensor systems and said one or more reference systems, it is obtained that the influences of drift of the intensity of the excitation source, photo-bleaching of active component of the sensor, and drift in the detector efficiency on the phase detector outputs on said one or more phase output signals are reduced whereby an improved apparatus for measuring concentration of one or more analytes is obtained.

Conversion of said one or more phase output signals to concentration measures are known in the art, see e.g. Lakowicz, Joseph R., Principles of fluorescence spectroscopy, Second Edition, Kluwer Academic/Plenum Publishers, New York 1999.

In general, conversion factors are based on calibration of phase output signals produced by samples containing known analytes including known concentrations of the analytes of interest. Also, conversion factors can be based on absolute calibration using physical and chemical parameters of the sample and analytes.

Conversion factors are typically stored and retrieved for phase-to-concentration conversion by means known in the art, e.g. by computer and electronic storage media.

Preferred embodiments are defined in the sub claims.

Reference Systems

According to the present invention, the one or more reference systems each comprise one or more passive reference light sources and are adapted to produce one or more electrical reference output signals in response to said one or more excitation signals.

Generally, the reference light source can be any suitable reference light source which varies in a similar manner as the fluorescence sensors do with respect to all influences thereon except that of the one or more analytes.

Reference light sources can be passive or active. Passive light sources are preferred as they usually involve fewer sources of variability.

In a preferred embodiment, said one or more reference systems comprise a fluorophore, a phosphore, or both whereby reference systems having very similar behaviour as the sensor systems can be designed.

For examples, for reference systems wherein the passive reference light source comprises a fluorophore, e.g. fluorescein derivatives, rhodamin derivatives, or both, that are encapsulated in e.g. nano- or microparticles for shielding from influence of the environment, the response of the reference light source can be made similar to that of the fluorescence system for one or more analytes. As the fluorophore shifts the reference wavelength, this solution also reduces straylight at the excitation wave-length.

In another preferred embodiment, said one or more reference system comprise one or more reflectors, said reflectors reflecting said light of said one or more excitation light sources. This embodiment provides a particularly simple reference light source for many applications. Further, this reference light source does not depend on the effect of the surroundings of the analyte on the fluorescence sensors.

The reflectors of the reference system can be of any suitable form that provides reflection. In still another preferred embodiment, said one or more reflectors comprise of a diffuse reflector, a retro-reflector, or both, whereby a reference system highly insensitive to changes in the spatial radiation characteristics of the excitation source is obtained.

In a particularly preferred embodiment, said one or more reflectors comprise a mirror whereby a high level of optical control of the reference light is obtained, minimising the influence of straylight.

In still a further preferred embodiment, said one or more reference systems are placed close to said one or more sensor systems whereby most equal conditions are met for both the fluorescence sensors and the references, and the accuracy of the referencing is further improved.

Phase Detectors

According to the present invention, there is provided one or more phase detectors, said phase detectors being adapted to detect one or more delays of said one or more electrical output signals of said one or more fluorescence sensor systems and said one or more reference systems, and to produce one or more phase output signals.

Phase detectors are known in the art, see e.g. Stanford Research Systems Catalogue 1998, Application Note #3, "About Lock-in Amplifiers" pp. 193-204, the content of which is hereby incorporated by reference.

One or More Excitation Light Sources

The one and more excitation light sources comprise light source which is able to excite fluorophores and/or phosphores of the sensor systems.

An important parameter of the excitation light is its wavelength. In some applications the fluorescence sensor can be designed, so that all sensor systems can utilize the same excitation light source, in particular in case of multiple wavelength of the same light source.

In a preferred embodiment, the apparatus comprises one or more single excitation light sources for said sensor systems and reference systems.

In some applications, the single excitation light source might not comprise the required multiple wavelengths which can excite the desired fluorophores and phosphores. Consequently, more than one excitation source is required.

In another preferred embodiment, the apparatus comprises one excitation light source for each sensor system and each reference system whereby optimum excitation efficiencies can be obtained for each fluorescence sensor.

The one or more excitation light sources can be operated in time domain, frequency domain or both.

In a preferred embodiment, said one and more light sources comprise at least one excitation light source adapted to operate in frequency domain.

Fluorescence Sensors-Sensor Chemistry

The fluorescence sensor can be in any suitable form wherein the analytes can be sensed by the fluorescence sensor chemistry and provide a characteristic emission of fluorescence light of the fluorophore in response of the presence of an analyte and the excitation light.

In a preferred embodiment, the one or more fluorescence sensors for sensing the one or more analytes are incorporated in an exchangeable sensor cap whereby sensors can be designed for the same system of excitation light sources, reference system, and phase detectors.

Generally, in the present context it is intended that the term fluorophore designates both fluorophore and phosphore, respectively.

Consequently, in a preferred embodiment, the one or more sensors for sensing the one or more analytes comprise a fluorophore, a phosphore, or both.

Fluorescence sensor chemistry is known in the art, see e.g. Wolfbeis Otto S. et. al., "Set of luminescence decay time based chemical sensors for clinical applications", Sensors and Actuators B, Vol. 51, 1998, p. 17-24

Fluorescence Sensor Systems

The fluorescence sensor systems can be designed in any suitable way that allows one or more fluorescence sensors to sense one or more analytes, when brought into contact therewith, and to receive one or more excitation signals to produce one or more electrical output signals in response thereto. The one or more electrical output signals are delayed with respect to said one or more excitation signals and they are characteristic of the fluorescence lifetimes of the one or more fluorescence sensors.

Preferred embodiments of the fluorescence sensor systems depend on the application.

In a preferred embodiment, the one or more fluorescence sensors for sensing the one or more analytes are incorporated in an exchangeable sensor cap whereby a sensor system which is easy to exchange is provided. This is advantageous for easy and fast exchange of sensor chemistry when damaged, or if the configuration of the sensor is to be altered for sensing of different analytes.

Particularly, said one or more fluorescence sensors for sensing the one or more analytes comprise a fluorophores, a phosphore, or both.

In another preferred embodiment, said one or more sensor systems comprise one or more sensors, one or more detectors, and one or more waveguides between said one or more sensors and detectors whereby a particular compact, robust multi-analyte sensor can be provided.

In still another embodiment, said one or more sensor systems comprise one or more light directing means, said light directing means directing said one or more excitation light signals to said one or more sensors.

In still another embodiment, said one or more light directing means consist of one or more reflective cones whereby a particular simple means of directing excitation light to the fluorescence sensors is provided.

In still another embodiment, said one or more light directing means consist of one or more diffractive optical elements whereby a particular compact apparatus can be provided.

Application Systems

The apparatus according to the present invention can be implemented in any suitable way that allows said fluorescence sensor systems and reference systems to become implemented.

The present invention can be utilized within a large variety of application areas, including but not limited to, wastewater cleaning plants, drinking water processing, industrial fermentation tanks, general food processing, modified atmosphere packed food (MAP), micro-reactor scanning systems, tissue engineering, etc.

In a preferred embodiment, said one or more sensor systems and said reference system are incorporated in a flow cell whereby a fluid or gas flowing continuously can be monitored for multiple analytes.

In another preferred embodiment, said one or more sensor systems and said reference system are incorporated in a micro bioreactor whereby previously unavailable on-line monitoring of multiple analytes becomes possible.

In still another preferred embodiment, said one or more sensor systems and said reference system are incorporated in a micro fluid-channel system.

In still another preferred embodiment, said one or more sensors of the sensor systems are wholly or partially covered with one or more semi-permeable membranes. Such membranes can be silicone or Teflon membranes for measuring gaseous or other neutral species and for improving the selectivity (gas permeable but with ion shielding properties). In addition, such membranes can include black analyte-permeable layers to improve photostability to shield the sensor from intrinsic sample fluorescence, and to avoid a too high level of ambient light Time-Resolved Fluorescence Measurement There is basically two ways of performing time-resolved fluorescence measurements: time-domain and frequency-domain measurements (see e.g. Lakowicz, Joseph R., Principles of fluorescence spectroscopy, Second Edition, Kluwer Academic/Plenum Publishers, New York 1999).

Time-resolved fluorescence measurements utilise a short pulse for excitation of the fluorophore and the decay of the fluorescence light from the fluorophor is then measured. This technique requires a light source capable of emitting very short pulses of light and very fast sampling detection electronics.

Frequency-domain measurements utilize a continuously modulated light source for exciting the fluorophore. The fluorescence emitted from the fluorophore will then be delayed compared to the excitation light due to the fluorescence lifetime of the fluorophor. This delay can be measured as a phase shift between the excitation light and the emitted fluorescence. This technique is advantageous for mass produced sensors compared to the time-domain technique, as both the excitation light source and the detection electronics are significantly cheaper.

Fluorescence Lifetime Sensing Device Comprising an Optical Light Beam-Adapting System which Comprises a Reflective Surface In still another aspect according to the present invention, these objects are fulfilled by providing a fluorescence lifetime sensing device for sensing fluorescence lifetimes of fluorescence sensors for one or more analytes, the sensor device comprising:

a fluorescence sensor system comprising one or more fluorescence sensors, said sensors being adapted to sense the one or more analytes and produce fluorescence light in response thereto;

a phase reference system comprising a passive reference light source;

an optical light beam-adapting system providing excitation lights for the fluorescence sensors and reference light for said phase reference system;

a detection system comprising detectors for detecting said fluorescence light from said fluorescence sensors and reference light from said phase reference system; and an optical sensor and reference signal guiding system, said guiding system guiding said fluorescence light and said reference light to said detectors;

wherein said optical light beam-adapting system comprises a reflective surface directing said excitation light to the fluorescence sensors and said reference light to said phase reference system.

It turns out that when said optical light-beam adapting system comprises a reflective surface directing said excitation light to the fluorescence sensors and said reference light to said phase reference system, a particular simple and robust sensing device can be provided.

The reflective surface can be any reflective surface that is able to direct said excitation light to said fluorescence sensors and said reference light to said phase reference system.

In a preferred embodiment, said reflective surface comprises the outer surface of a cone whereby a particularly simplified multi-analyte sensor can be provided.

In another preferred embodiment, the optical light beam-adapting system comprises optical fibres whereby said excitation light and reference light can easily be guided to the fluorescence sensor and phase reference system, respectively. Furthermore, utilization of optical fibres for transport of excitation light enables remote location of the excitation source in relation to the detectors, reducing excitation source induced electromagnetic noise in the detection circuits.

Similarly, in another preferred embodiment, said optical sensor and reference signal guiding system comprises optical fibres, whereby a particular effective lightguiding system is obtained, reducing the photo-bleaching of the sensor chemicals as they can then provide sufficient signal with less excitation light.

In a preferred embodiment, this sensing device comprises one or more phase detectors as defined for the apparatus according to the present invention; said phase detectors being adapted to detect one or more delays of said one or more electrical output signals of said one or more fluorescence sensor systems and said one or more reference systems, and to produce one or more phase output signals.

Fluorescence Lifetime Sensing Device Comprising One or More Fluorescence Sensors Incorporated in an Exchangeable Cap In still another aspect according to the present invention, these objects are fulfilled by providing a fluorescence lifetime sensing device for sensing fluorescence lifetimes of fluorescence sensors for one or more analytes, the sensor device comprising a fluorescence sensor system comprising one or more fluorescence sensors, said sensors being adapted to sense the one or more analytes and produce fluorescence light in response thereto;

a phase reference system comprising a passive reference light source;

an optical light beam-adapting system providing excitation lights for the fluorescence sensors and reference light for said phase reference system;

a detection system comprising detectors for detecting said fluorescence light from said fluorescence sensors and reference light from said phase reference system; and an optical sensor and reference signal guiding system, said guiding system guiding said fluorescence light and said reference light to said detectors;

wherein said one or more fluorescence sensors are incorporated in an exchangeable cap.

It turns out that when said one or more fluorescence sensors are incorporated in an exchangeable cap, a particular flexible sensing device with low operating costs can be provided.

In a particularly preferred embodiment, said reference light source is incorporated in said exchangeable cap whereby said fluorescence sensors and said reference light source can be brought closely together and provide an improved referencing with approximately similar conditions for the fluorescence sensor and the reference.

In a preferred embodiment, this sensing device comprises one or more phase detectors as defined for the apparatus according to the present invention; said phase detectors being adapted to detect one or more delays of said one or more electrical output signals of said one or more fluorescence sensor systems and said one or more reference systems, and to produce one or more phase output signals.

Fluorencence Lifetime Sensing Device Comprising an Optical Light Beam-Adapting System and an Optical Sensor and Reference Signal Guiding System One of Which, or Both, are Incorporated in an Diffractive Optical Element In still another aspect according to the present invention, these objects are fulfilled by providing a fluorescence lifetime sensing device for sensing fluorescence lifetimes of fluorescence sensors for one or more analytes, the sensor device comprising a fluorescence sensor system comprising one or more fluorescence sensors, said sensors being adapted to sense the one or more analytes and produce fluorescence light in response thereto;

a phase reference system comprising a reference light source;

an optical light beam-adapting system providing excitation lights for the fluorescence sensors and reference light for said phase reference system;

a detection system comprising detectors for detecting said fluorescence light from said fluorescence sensors and reference light from said phase reference system; and an optical sensor and reference signal guiding system, said guiding system guiding said fluorescence light and said reference light to said detectors;

wherein said optical light beam-adapting system, said optical sensor and reference signal guiding system, or both, are incorporated in an diffractive optical element.

It turns out that when said optical light beam-adapting system, said optical sensor and reference signal guiding system, or both, are incorporated in a diffractive optical element, a particular compact sensing device can be provided. Furthermore, this design reduces the number of components which lower production cost and increase reliability.

Diffractive optical elements can be produced by methods known in the art, see e.g. Babin, S. V. "Data preparation and fabrication of DOE using electron-beam lithography", Optics and Lasers in Engineering, Vol. 29 Issue 4-5, 1998, pp. 307-324, and Taghizadeh, M. R. et al. "Design and fabrication of diffractive optical elements", Microelectronic Engineering, Vol. 34, Issue 3-4, 1997, pp. 219-242.

In a preferred embodiment, said optical light beam-adapting system comprises a stacked planar integrated optical layer structure which is especially advantageous for mass production.

Stacked planar integrated optical layer structures can be produced by methods known in the art, see e.g. Sinzinger, S. J. J "Microoptics", Wiley-VCH, 1999.

In a particularly preferred embodiment, said layer structure comprises an electronic layer, a detector layer, a light source, a diffractive optical element, a sensor and reference layer and a filter layer.

In a preferred embodiment, this sensing device comprises one or more phase detectors as defined for the apparatus according to the present invention; said phase detectors being adapted to detect one or more delays of said one or more electrical output signals of said one or more fluorescence sensor systems and said one or more reference systems, and to produce one or more phase output signals.

Method of Measuring Concentration

In another aspect of the present invention there is provided a method of measuring the concentration of one or more analytes, the method comprising (a) providing an apparatus as defined according to the invention, or a device according to the invention;

(b) applying said one or more excitation light signals to said one or more fluorescence sensor systems and to said one or more passive reference light sources;

(c) applying said one or more electrical output signals of said one or more fluorescence sensor systems and said one or more reference systems to said one or more phase detectors;

(d) determining said one or more delays by said one or more phase output signals; and (f) comparing said one or more determined delays with delay calibration data of known concentrations of the one or more analytes, whereby particular accurate concentration measurements can be obtained.

Fluorescence Lifetime Measurement

Measurements of fluorescence lifetime are known in the art. They include measurements in the time-domain and/or frequency domain, see e.g. Lakowicz, Joseph R., Principles of fluorescence spectroscopy, Second Edition, Kluwer Academic/Plenum Publishers, New York 1999.

In a preferred embodiment, the present invention is based on frequency domain measurement which allows a robust and inexpensive technique to be implemented with less stringent component demands compared to the time-domain technique.

In particular, phase referencing according to the present invention allows very accurate determination of the phase of the excitation source whereby phase resolutions in the order of fractions of a degree can be obtained.

Consequently, fluorescent lifetime measurements based on frequency domain and referencing according to the present invention provide a number of advantages.

Firstly, intensity drift in the excitation source and drift in the efficiency of the detectors do not affect the measurements. Secondly, photo-bleaching of the fluorophores only limits the total lifetime of the sensor, and not the measurements. The sensor is operational as long as there is provided a sufficiently high signal compared to the noise in the system. The need for re-calibration due to photo-bleaching is therefore strongly reduced, which is very important in e.g. industrial process monitoring applications where sensor systems are to be operated continuously for long periods of time.

Fluorescence lifetime measurements of multi-analyte sensors may be combined with other techniques for sensing analytes such as techniques based on intensity, polarisation, optical rotation, etc.

BRIEF DESCRIPTION OF THE DRAWINGS

In the following, by way of examples only, the invention is further disclosed with detailed description of preferred embodiments. Reference is made to the drawings in which.

DETAILED DESCRIPTION

Figure 1:
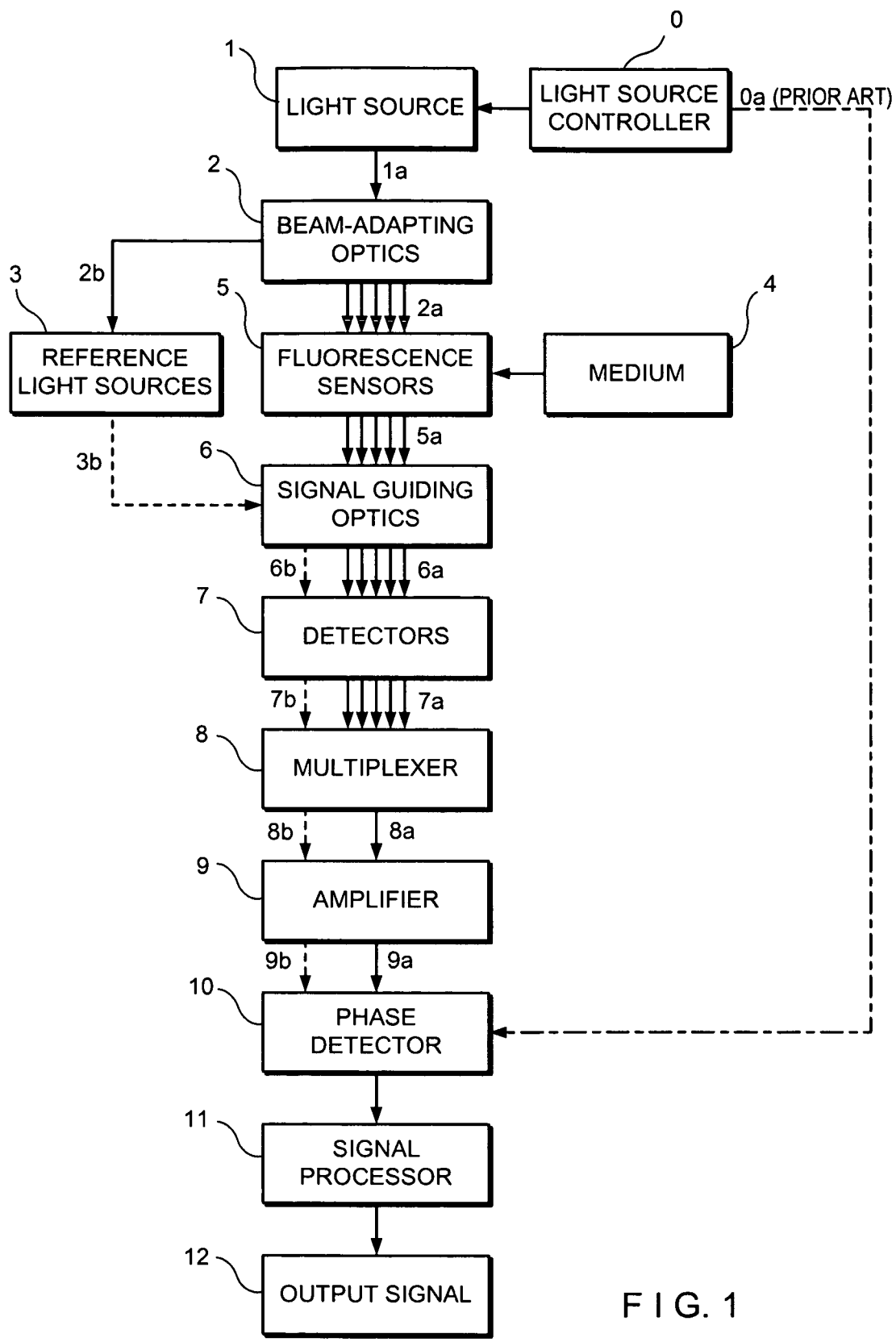
FIG. 1 shows a flow chart diagram of information flow in a multi-analyte sensor device according to an embodiment of the present invention.

FIG. 1 shows a flow chart diagram of information flow within a multi-analyte sensor device according to an embodiment of the present invention.

A light source controller 0 feeds a control signal to a light source 1 producing one or more excitation signals 1a. Beam-adapting optics 2 provide beam-adapted excitation lights 2a,2b to a fluorescence sensor system 5,6,7 and a reference system 3,6,7, respectively, said beam-adapting optics generally being optional. It is preferred, however, to include beam-adapting optics to more efficiently guide excitation light to said fluorescence sensor and reference systems. A medium 4 comprises analytes to be determined, e.g. $O_2$, $CO_2$, pH, and ions determining salinity, in particular salt ions such as $Na^+$ and $Cl^-$, and temperature. The reference system comprising reference light sources 3, e.g. a fluorophore, phosphore, or both, or one or more reflectors, which are not influenced by the one or more analytes to any significant degree for the measurement and the fluorescence sensor system comprising fluorescence sensors 5 for sensing said analytes in the medium provide optical signals 3b and 5a, respectively, to signal guiding optics 6. Detectors 7 detect light signals 6a and 6b from said light guiding optics that originated from the fluorescence sensors 5 and the reference light sources 3, respectively. The detectors 7 produce electrical output signals 7a and 7b corresponding to the fluorescence sensors 5 and phase reference system 3, respectively. Optionally, e.g. instead of parallel channels, a multiplexer 8 selects sensor signals 8a and the reference signals 8b, respectively, for further processing. Optionally, an amplifier 9 amplifies said signals 8a, 8b from the multiplexer. A phase detector 10 detects the delays between said one or more electrical output signals, specifically here the delay between the amplified, selected electrical output signal 9a of the selected fluorescence sensor and the amplified electrical signal 9b of the reference system. Here signal processor 11 further treats the output signal of the phase detector and produces an output signal 12.

Referencing according to the present embodiment differs from that of the prior art in the phase reference system 3. According to the prior art a reference signal 0a (not part of the present embodiment according to the invention) from the light source controller 0 is fed to the phase detector 10 whereby drift and other contributions to the signal information in the various units 1,2, and 6-9 are not accounted for.

Compared with this prior art, the present invention provides a series of reference signals 2b, 3b, and 6b-9b that are influenced by all the contributions of drift, etc. from the units 1, 2, and 6-9.

Figure 2:
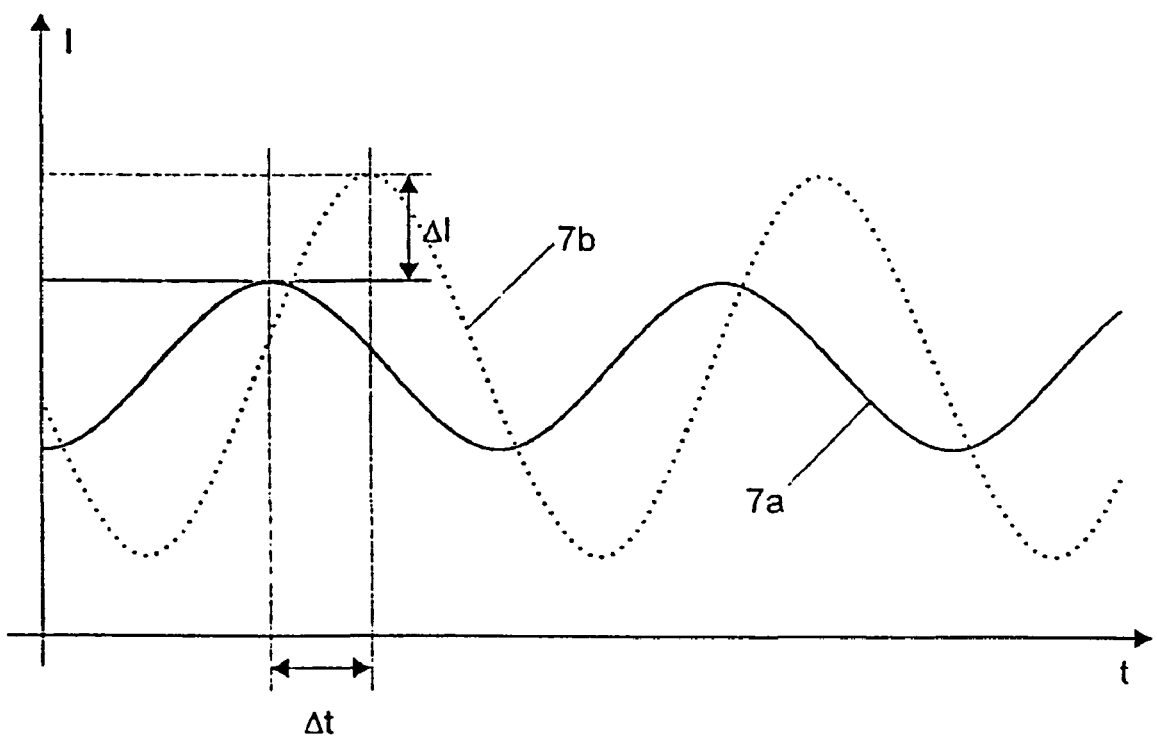
FIG. 2 illustrates delay between an electrical sensor output signal and a phase reference signal infrequency domain fluorescence lifetime measurement.

FIG. 2 illustrates time delay $\Delta t$ between an electrical sensor output signal 7a and a phase reference signal 7b in frequency domain fluorescence lifetime measurement. Further, FIG. 2 illustrates the modulation $\Delta l$ of the amplitude defined as the difference in amplitude at the time delay $\Delta t$.

Phase detection techniques are known in the art, see e.g. Stanford Research Systems Catalogue 1998, Application Note #3, "About Lock-in Amplifiers" pp. 193-204, the content of which is hereby incorporated by reference.

Figure 3:
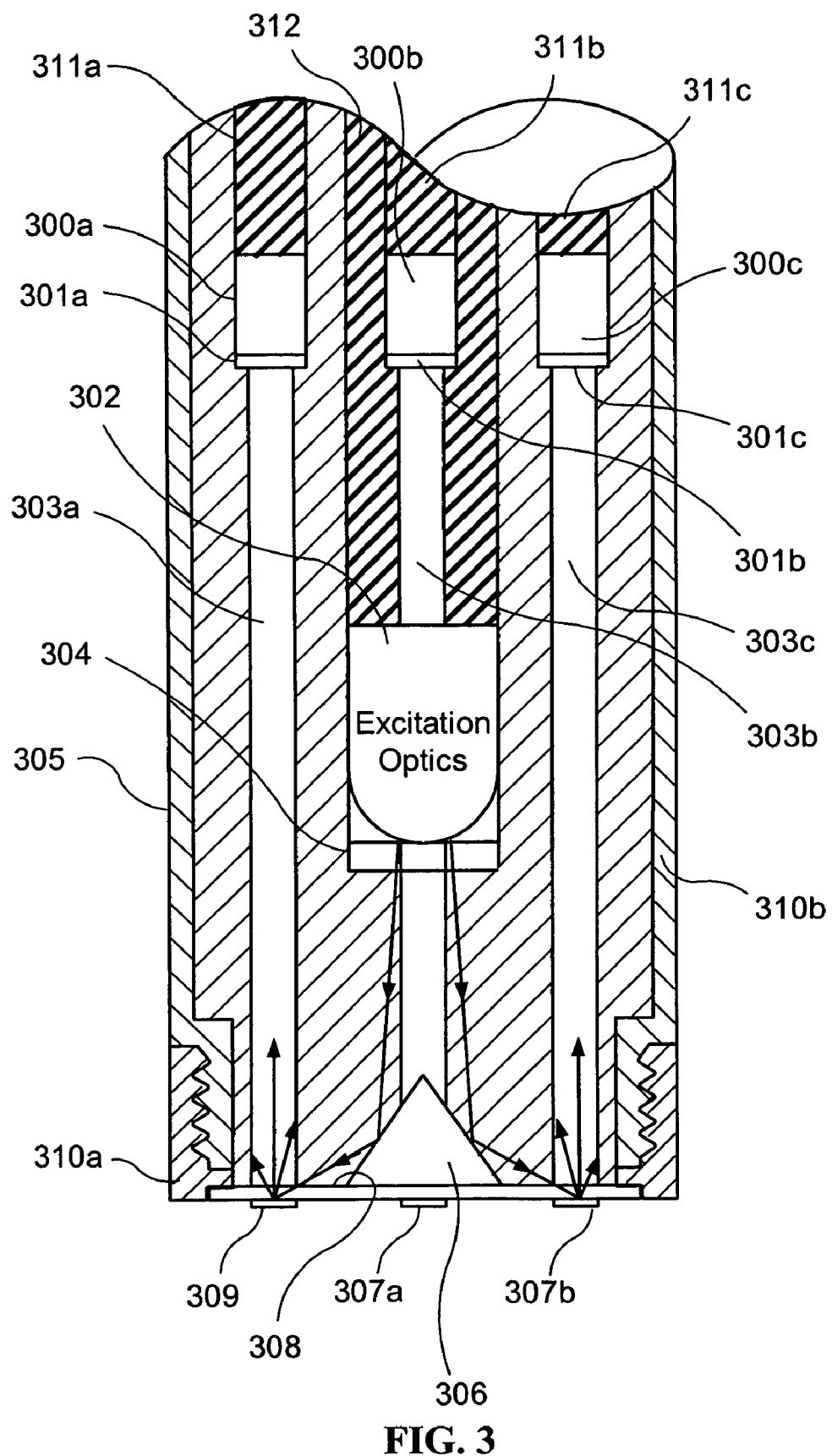
FIG. 3 illustrates a preferred embodiment of a fluorescence sensor and reference system in a longitudinal cross sectional view.
Figure 4A:
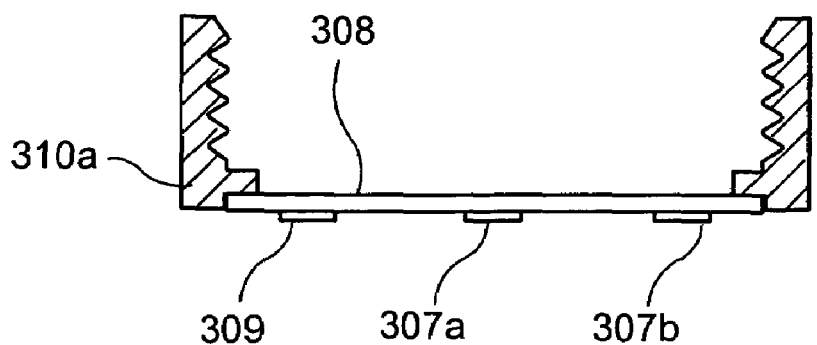
FIGS. 4A-4C illustrate a preferred embodiment of an exchangeable sensor cap illustrated in FIG. 3.
Figure 4B:
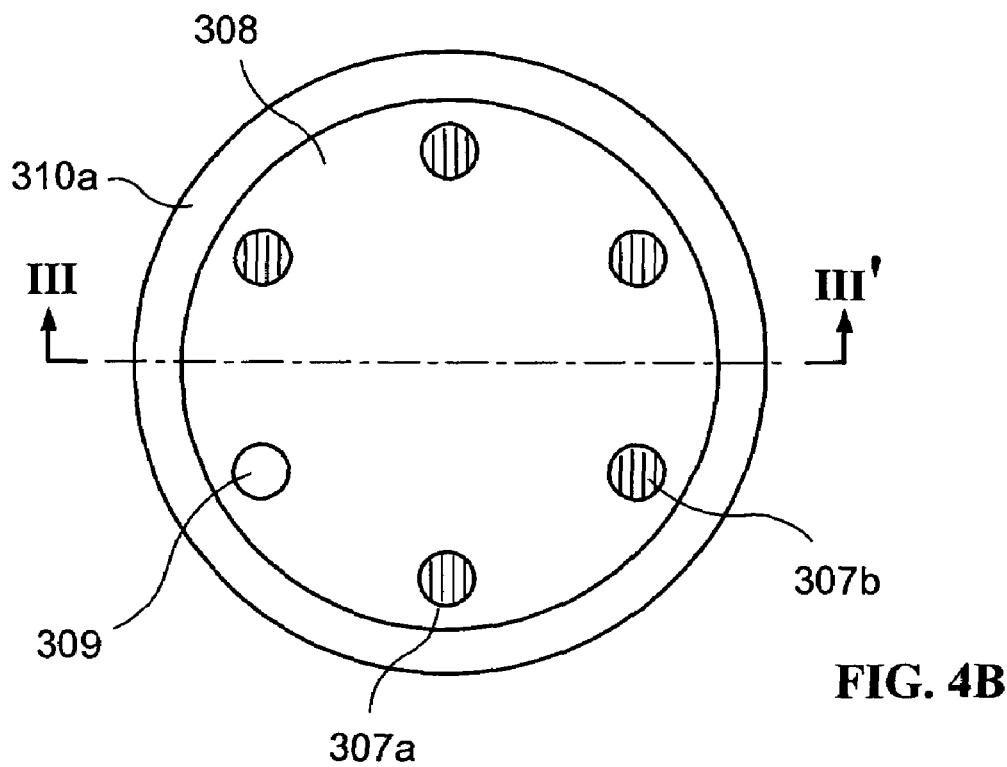

FIG. 3 illustrates a preferred embodiment of a fluorescence sensor and reference system in a longitudinal side view of cross sectional along line III-III (see FIG. 4B)

A cylindrical housing 310b is assembled with a sensor cap comprising a sensor holder 310a and sensor lid 308 combination, here illustrated with a screwed female-male threading fixing the housing and cap together. Other fixation techniques can be used e.g. adhesion, welding, and mechanical latching such as snap-lock latching.

Here, the exchangeable sensor cap accommodates fluorescence sensors 307a and 307b, e.g. $pO_2$ (Lifetime: Ru[dpp]) and pH (Dual Lifetime Referencing (DLR): Fluorescein and Ru[dpp]), respectively and reference system 309, e.g. comprising a mirror as the passive reference light sources. It can be exchanged when damaged, or reconfigured with different fluorescence sensors and reference systems, when other or new applications are required.

The housing accommodates an excitation light source, here illustrated by a light emitting diode (LED) 302 having a predominant emission at 470 nm, e.g. an InGaN-based LED from Agilent (HLMP-CB15/16), and positioned in the centre of the housing, and an optional excitation filter 304 for selecting one or more wavelengths of interest, here a typical 480 nm low pass filter is used. Suitable optical filters can be filters based on interference, absorption, or both, or based on any other non-fluorescent type filter.

The excitation light source is preferably adapted to transmit light in a predetermined direction, e.g. by optically shielding off unwanted light to the optical waveguides collecting the emitted fluorescence light from the fluorescence sensors.

Light sources of the solid-state type are preferred for many applications because they might be superior to e.g. flash lamps, as they are smaller, cheaper, have longer lifetimes, and can be modulated directly through a bias-current.

Generally, the excitation optics comprises traditional lenses, diffractive optical elements (DOE), fibres, diffusers, and any combination of beam-shaping optics, alone or in combination.

The LED is modulated at 45 kHz, which is a suitable modulation frequency for most applications.

A light directing means, here illustrated by a reflective cone 306 is positioned to receive excitation light at its outer surface and direct it through reflection to fluorescence sensors, here illustrated by fluorescence sensors 307a and 307b mounted on the outer side of a cap lid 310c, and direct it to the reference system, here illustrated by a mirror of reference system 309 mounted on the outer side of a cap lid 308 and functioning as a passive reference light source.

Fluorescence light from the fluorescence sensors, here fluorescence sensors 307a and 307b positioned in the lid 308 of the exchangeable sensor cap, is guided through optical wave guides, here optical fibres 303a, 303b, and 303c, to detectors 300a, 300b, and 300c, here solid-state photodiodes in front of which optical filters 301a, 301b, 301c are placed in order to reduce stray-light induced errors.

The various components, here excitation light source 302, light directing means 306, optical wave guides 303 and detectors are embedded in a solid body thereby providing a sensing device which is rugged and insensitive to vibrations and shock.

The solid body comprises inserts for wave-guides 311a, 311b, 311c and detectors and an insert for the excitation light source 312.

The sensor body material is chosen to be transparent in the excitation wavelength region e.g. around 470 nm. Suitable materials are known in the art including polymers like polycarbonate and polystyrene.

Furthermore, the solid body design eliminates optics/air interfaces at which possible dew formations from operation in humid environments might disturb the signal and signal loss due to reflections are minimized.

The fluorescence light is emitted isotropically from the fluorescence sensors. It is therefore important that the collection system can detect the emitted fluorescence light under as large an angle as possible. Here, high NA plastic fibres preferably collect the emitted fluorescence light. Collection of the emitted fluorescence light in this way ensures that a high light collection efficiency is obtained whereby it possible to excite the fluorescence sensors with light of lower intensity to obtain a comparable fluorescence light signal and thereby to diminish photo-bleaching and prolong the lifetime of the fluorescence sensors.

Figure 4C:
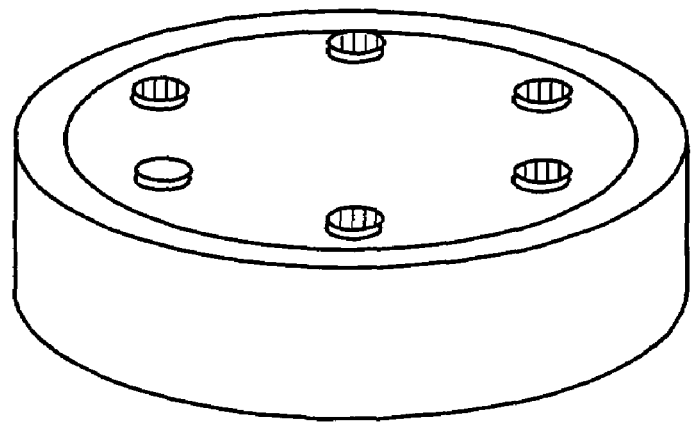

FIGS. 4A-4C illustrate a preferred embodiment of an exchangeable sensor cap illustrated in FIG. 3.

FIG. 4A shows a longitudinal sectional view of the sensor cap along the line III-III (see FIG. 4B). The sensor cap comprises a cap lid 308 fixed to a sensor holder 310a with male screw threadings. Fluorescence sensors 307a and 307b and reference system 309 are fixed to the outer side of the cap lid.

FIG. 4B shows a bottom view of the sensor cap comprising a sensor holder 310a and cap lid 308 to the surface of which fluorescence sensors 307a and 307b are fixed.

FIG. 4C shows a perspective view of the sensor cap.

Specific sensors capable of measuring pH, $O_2$, $CO_2$, salinity and temperature by utilizing 5 different kinds of fluorescent sensor chemistries—three of them based on the Dual Lifetime Referencing (DLR) technique and 2 of them true fluorescence lifetime sensors—all available from PreSens, Regensburg, Germany:

$PO_2$ (Lifetime: Ru[dpp])
pH (DLR: Fluorescein and Ru[dpp])
$pCO_2$ (DLR: HPTS and Ru[dpp])
Salinity (DLR: Lucigenin and Ru[dpp])
Temperature (Lifetime: Ru[phen])

For DLR and the specific fluorescence sensors and other useful sensors see WO99/06821 the content of which is incorporated herein by reference.

Figure 5A:
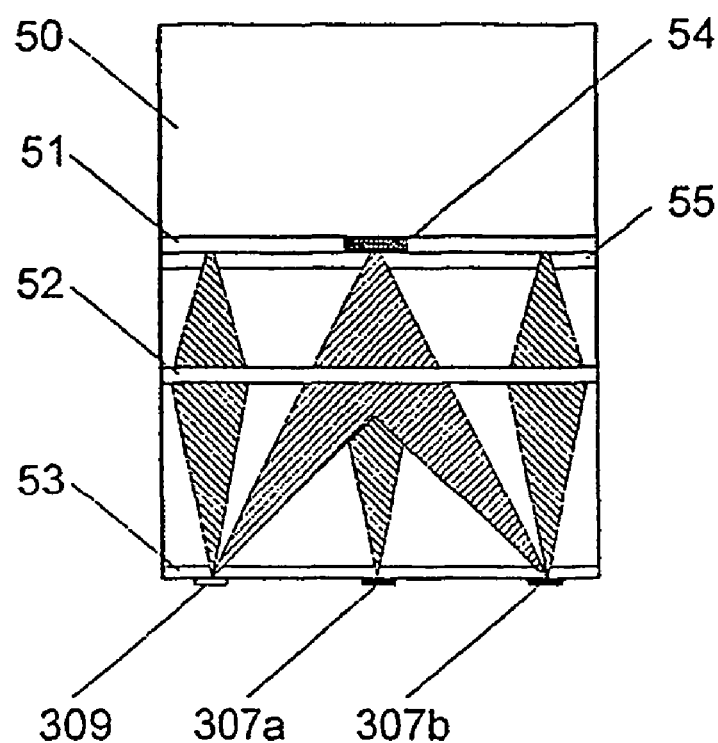
FIGS. 5A and 5B illustrate another preferred embodiment of a fluorescence sensor system and a reference system comprising diffractive optical elements and stacked planar integrated optics.
Figure 5B:
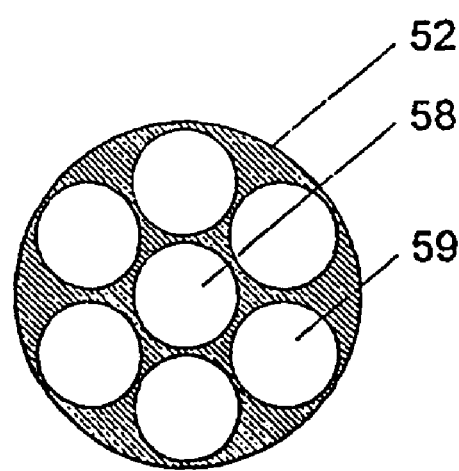

FIGS. 5A and 5B illustrate another preferred embodiment of a fluorescence sensor system and a reference system comprising diffractive optical elements and stacked planar integrated optics which are particularly suited for cheap mass production.

The sensor is divided into multiple layers which can be produced on wafers, stacked and sliced dramatically reducing production cost and time (see e.g. Sinzinger, S. J. J "Microoptics", Wiley-VCH, 1999).

The sensor comprises 4 primary layers: a sensor and reference layer 53 comprising fluorescence sensors and phase reference system, here including a mirror, a diffractive optical element layer 52 optionally further comprising one or more conventional optical elements such as lenses, diffusers, prisms, beam splitters, and coatings, a filter layer 55 and a detector layer 51, and an excitation light source 54, here a light emitting diode, located above the detector layer, and an electronic layer 50, here coupled to the detector layer 51.

The detector and filter layer can be combined in a common layer, if the filters are deposited directly on the detector layer.

The diffractive optical element is divided into two main sections: a centre section 58 and a circumference section 59.

The centre section comprises diffractive gratings adapted to focus light from excitation light source onto the different fluorescence sensors and the phase reference system.

The circumferential section comprises a section for each fluorescence sensor and one for the phase reference system. Each section comprises diffractive gratings adapted for collecting light from the fluorescence sensors and phase reference system and for focussing the collected light through the filter layer 55 and further on to the detector layer 51.

Diffractive optical elements are known in the art, see e.g. Babin, S. V. "Data preparation and fabrication of DOE using electron-beam lithography", Optics and Lasers in Engineering, Vol. 29 Issue 4-5, 1998, pp. 307-324, and Taghizadeh, M. R. et al. "Design and fabrication of diffractive optical elements", Microelectronic Engineering, Vol. 34, Issue 3-4, 1997, pp. 219-242.

Figure 6A:
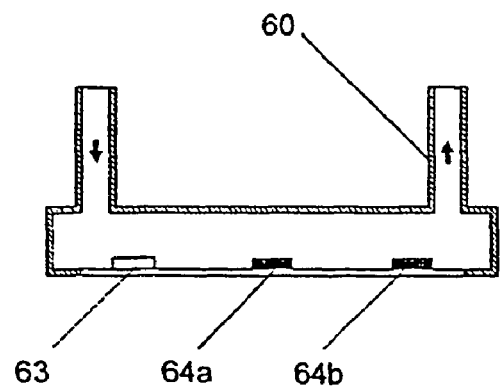
FIGS. 6A-6C illustrate different applications of multi-analyte sensor devices according to the invention.

FIG. 6a shows a flow cell 60, where sensor chemicals of the fluorescence sensors 64a, 64b and reference 63 are applied to the wall thereof. The chemicals are excited through a transparent section of the flow cell through which the fluorescence light is also detected.

Figure 6B:
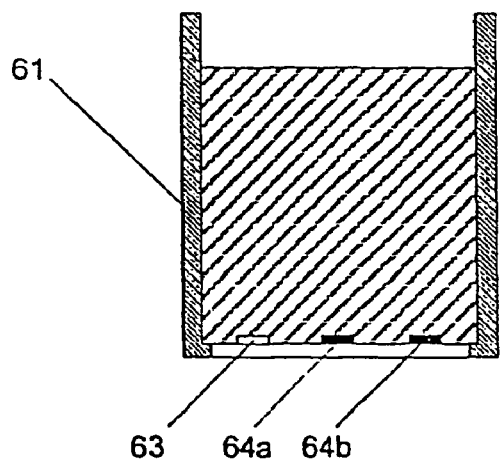

FIG. 6b illustrates a micro bioreactor 61 with sensor chemicals applied to the transparent bottom. The processes in the reactor can then be monitored from below with one of the sensor systems previously described.

Figure 6C:
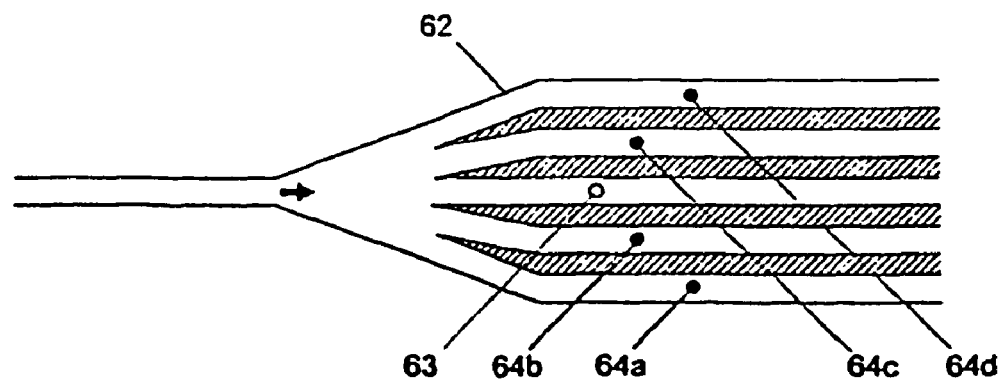

FIG. 6c shows a micro fluid channel system 62 allowing continuously monitoring of very small liquid volumes.

The invention claimed is:

1. An apparatus for measuring fluorescence lifetimes of fluorescence sensors for one or more analytes, the apparatus comprising (a) one or more excitation light sources, said light sources being adapted to produce one or more excitation signals;

(b) one or more fluorescence sensor systems, said sensor systems each comprising one or more fluorescence sensors for sensing the one or more analytes and being adapted to receive said one or more excitation signals to produce one or more optical sensor signals in response thereto, and to produce one or more electrical output signals in response to said optical sensor signals, said one or more electrical output signals being delayed with respect to said one or more excitation signals and being characteristics of the fluorescence lifetimes of the one or more fluorescence sensors;

(c) one or more reference systems, said reference systems each comprising one or more reference light sources and being adapted to receive said one or more excitation signals to produce reference optical signals in response thereto, and to produce one or more electrical reference output signals in response to said one or more optical reference signals; and (d) one or more phase detectors, said phase detectors being adapted to detect one or more delays of said one or more electrical output signals of said one or more fluorescence sensor systems and said one or more reference systems, and to produce one or more phase output signals;

wherein said one or more fluorescence sensors and said one or more reference light sources are incorporated in an exchangeable sensor cap.

2. The apparatus according to claim 1 wherein said one or more reference light sources comprise a fluorophore, a phosphore, or both.

3. The apparatus according to claim 1 wherein said one or more reference light sources comprise one or more reflectors, said reflectors reflecting said light of said one or more excitation light sources.

4. The apparatus according to claim 3 wherein said one or more reflectors comprise a diffuse reflector, a retro-reflector, or both.

5. The apparatus according to claim 3 wherein said one or more reflectors comprise a mirror.

6. The apparatus according to claim 1 comprising a single excitation light source for said sensor systems and reference systems.

7. The apparatus according to claim 1 comprising a plurality of excitation light sources each for respective ones of the sensor systems and reference systems.

8. The apparatus according to claim 1 wherein the one or more fluorescence sensors for sensing the one or more analytes comprise a fluorophore, a phosphore, or both.

9. The apparatus according to claim 8 wherein the one or more analytes are selected from the group consisting of $O_2$, $CO_2$, pH, ions from an ionic compound, and temperature.

10. The apparatus according to claim 1, wherein said one or more fluorescence sensor systems comprise one or more fluorescence sensors, one or more detectors, and one or more wave guides between said one or more fluorescence sensors and detectors.

11. The apparatus according to claim 1, wherein said one or more fluorescence sensor systems comprise one or more light directing means, said light directing means directing said one or more excitations light signals to said one or more fluorescence sensors and reference light source.

12. The apparatus according to claim 11 wherein said one or more light directing means comprise one or more reflective cones.

13. The apparatus according to claim 11 wherein said one or more light directing means comprise one or more diffractive optical elements.

14. The apparatus according to claim 1 wherein said one or more fluorescence sensor systems and said reference system are incorporated in a flow cell.

15. The apparatus according to claim 1 wherein said one or more fluorescence sensor systems and said reference system are incorporated in a micro bioreactor.

16. The apparatus according to claim 1 wherein said one or more fluorescence sensor systems and said reference system are incorporated in a micro fluid channel system.

17. The apparatus according to claim 1 wherein said one or more sensors of the sensor systems are wholly or partially covered with one or more semi-permeable membranes.

18. The apparatus according to claim 1 wherein said one or more excitation light sources comprise at least one excitation light source adapted to operate in frequency domain.

19. A fluorescence lifetime sensing device for sensing fluorescence light of fluorescence sensors for one or more analytes, the sensor device comprising
    a fluorescence sensor system comprising one or more fluorescence sensors said sensors being adapted to sense the one or more analytes and produce fluorescence light in response thereto;
    a phase reference system comprising a reference light source;
    an optical light beam-adapting system providing excitation lights for the fluorescence sensors and reference light for said phase reference system;
    a detection system comprising detectors for detecting said fluorescence light from said fluorescence sensors and reference light from said phase reference system; and
    an optical sensor and reference signal guiding system, said guiding system guiding said fluorescence light, and said reference light to said detectors;
    wherein said optical light beam-adapting system comprises a reflective surface directing said excitation light to the fluorescence sensors and said reference light to said phase reference system; and
    wherein the reflective surface is the outer surface of a cone.

20. The sensing device according to claim 19 wherein the optical light beam-adapting system comprises optical fibres.

21. The sensing device according to claim 19 wherein the optical sensor and reference signal guiding system comprises optical fibres.

22. A fluorescence lifetime sensing device for sensing fluorescence light of fluorescence sensors for one or more analytes, the sensor device comprising
    a fluorescence sensor system comprising one or more fluorescence sensors, said sensors being adapted to sense the one or more analytes and produce fluorescence light in response thereto;
    a phase reference system comprising a passive reference light source;
    an optical light beam-adapting system providing excitation lights for the fluorescence sensors and reference light for said phase reference system;
    a detection system comprising detectors for detecting said fluorescence light from said fluorescence sensors and reference light from said phase reference system; and
    an optical sensor and reference signal guiding system, said guiding system guiding said fluorescence light and said reference light to said detectors;
    wherein said one or more fluorescence sensors and said reference light source are incorporated in an exchangeable cap.

23. A fluorescence lifetime sensing device for sensing fluorescence light of fluorescence sensors for one or more analytes, the sensor device comprising
    a fluorescence sensor system comprising one or more fluorescence sensors, said sensors being adapted to sense the one or more analytes and produce fluorescence light in response thereto;
    a phase reference system comprising a reference light source;
    an optical light beam-adapting system providing excitation lights for the fluorescence sensors and reference light for said phase reference system;
    a detection system comprising detectors for detecting said fluorescence light from said fluorescence sensors and reference light from said phase reference system; and
    an optical sensor and reference signal guiding system, said guiding system guiding said fluorescence light and said reference light to said detectors;
    wherein said optical light beam-adapting system, and said optical sensor and reference signal guiding system, are incorporated in a diffractive optical element;
    and wherein said diffractive optical element comprises a first set of diffractive gratings adapted to focus light from an excitation light source onto respective ones of the fluorescence sensors and onto said phase reference system; and a second set of diffractive gratings adapted to collect light from respective ones of the fluorescence sensors and from the phase reference system and to focus the collected light onto said detectors.

24. The sensing device according to claim 23 wherein said optical light beam adapting system comprises a stacked planar integrated optical layer structure.

25. The sensing device according to claim 24 wherein said layer structure comprises an electronic layer, a detector layer, a light source, a diffractive optical element, a sensor and reference layer, and a filter layer.

26. A method of measuring concentration of one or more analytes, the method comprising
    (a) providing an apparatus as defined in claim 1;
    (b) applying said one or more excitation light signals to said one or more fluorescence sensor systems and to said one or more reference light sources;
    (c) applying said one or more electrical output signals of said one or more fluorescence sensor systems and said one or more reference systems to said one or more phase detectors;
    (d) determining said one or more delays by said one or more phase output signals;
    (e) comparing said one or more determined delays with delay calibration data of known concentrations of the one or more analytes, thereby obtaining a concentration value; and
    (f) outputting a signal representative of the concentration value.

27. A method of measuring concentration of one or more analytes, the method comprising
    (a) providing an apparatus as defined in claim 19;
    (b) applying said one or more excitation light signals to said one or more fluorescence sensor systems and to said one or more reference light sources;
    (c) applying said one or more electrical output signals of said one or more fluorescence sensor systems and said one or more reference systems to said one or more phase detectors;
    (d) determining said one or more delays by said one or more phase output signals;
    (e) comparing said one or more determined delays with delay calibration data of known concentrations of the one or more analytes, thereby obtaining a concentration value; and
    (f) outputting a signal representative of the concentration value.

28. A method of measuring concentration of one or more analytes, the method comprising
    (a) providing an apparatus as defined in claim 22;
    (b) applying said one or more excitation light signals to said one or more fluorescence sensor systems and to said one or more reference light sources;
    (c) applying said one or more electrical output signals of said one or more fluorescence sensor systems and said one or more reference systems to said one or more phase detectors;
    (d) determining said one or more delays by said one or more phase output signals;
    (e) comparing said one or more determined delays with delay calibration data of known concentrations of the one or more analytes, thereby obtaining a concentration value; and
    (f) outputting a signal representative of the concentration value.

29. A method of measuring concentration of one or more analytes, the method comprising
    (a) providing an apparatus as defined in claim 23;
    (b) applying said one or more excitation light signals to said one or more fluorescence sensor systems and to said one or more reference light sources;
    (c) applying said one or more electrical output signals of said one or more fluorescence sensor systems and said one or more reference systems to said one or more phase detectors;
    (d) determining said one or more delays by said one or more phase output signals;
    (e) comparing said one or more determined delays with delay calibration data of known concentrations of the one or more analytes, thereby obtaining a concentration value; and
    (f) outputting a signal representative of the concentration value.

* * * * *